US008308710B2

(12) United States Patent
Landman et al.

(10) Patent No.: US 8,308,710 B2
(45) Date of Patent: Nov. 13, 2012

(54) HIGH FLOW-LOW PRESSURE IRRIGATION SYSTEM

(75) Inventors: Jaime Landman, St. Louis, MO (US);
Ralph V. Clayman, Irvine, CA (US);
Richard C Ewers, Fullerton, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 2205 days.

(21) Appl. No.: 10/491,657

(22) PCT Filed: Aug. 29, 2002

(86) PCT No.: PCT/US02/27923
§ 371 (c)(1),
(2), (4) Date: Jan. 5, 2005

(87) PCT Pub. No.: WO03/033050
PCT Pub. Date: Apr. 24, 2003

(65) Prior Publication Data
US 2005/0107736 A1    May 19, 2005

Related U.S. Application Data (60) Provisional application No. 60/329,139, filed on Oct. 12, 2001.

(51) Int. Cl.
*A61M 25/00* (2006.01)
(52) U.S. Cl. .................. 604/523; 604/534; 604/544
(58) Field of Classification Search .................. 604/523, 604/534, 537, 27–39, 96.01, 164.01, 544
See application file for complete search history.

(56) References Cited

U.S. PATENT DOCUMENTS

| 697,181 A | 4/1902 | Smith |
| 3,091,242 A | 5/1963 | Johnson |
| 3,738,372 A | 6/1973 | Shioshvili |
| 4,111,209 A | 9/1978 | Wolvek |
| 4,154,245 A | 5/1979 | Daily |
| 4,259,961 A | 4/1981 | Hood, III |

(Continued)

FOREIGN PATENT DOCUMENTS

DE    3430095    2/1986

(Continued)

OTHER PUBLICATIONS

European Patent Office, Supplementary European Search Report for European Application No. 02801624 4, based on International Application No. PCT/US02127923, dated Jul. 1, 2008.

*Primary Examiner* — Kevin C Sirmons
*Assistant Examiner* — Phillip Gray
(74) *Attorney, Agent, or Firm* — Rimas T. Lukas; Patrick Y. Ikehara; Kenneth K. Vu (57) ABSTRACT

A high-flow low-pressure irrigation system for directing a fluid to and recovering the fluid from an area within a body, the irrigation system comprising a sheath defining a sheath lumen and a flexible catheter disposed in and through the sheath lumen. The catheter defines a catheter lumen and comprises a plurality of apertures at a distal portion that curls in a pigtail configuration. The fluid is directed and outputted to the body area through the catheter lumen and the apertures, and the outputted fluid is recovered and returned through the sheath lumen.

41 Claims, 5 Drawing Sheets

U.S. PATENT DOCUMENTS

| | | | |
|---|---|---|---|
| 4,468,216 A | | 8/1984 | Muto |
| 4,568,338 A | * | 2/1986 | Todd .............................. 604/530 |
| 4,573,979 A | | 3/1986 | Blake |
| 4,605,006 A | | 8/1986 | Jacques |
| 4,714,460 A | | 12/1987 | Calderon |
| 5,139,496 A | | 8/1992 | Hed |
| 5,364,340 A | | 11/1994 | Coll |
| 3,238,944 A | | 3/1996 | Hirschhorn |
| 5,558,634 A | | 9/1996 | Mitchell |
| 5,626,564 A | * | 5/1997 | Zhan et al. ............... 604/164.01 |
| 5,693,080 A | | 12/1997 | Wallsten |
| 5,702,368 A | | 12/1997 | Stevens et al. |
| 5,800,385 A | | 9/1998 | Demopulos |
| 5,800,486 A | | 9/1998 | Thome |
| 5,800,487 A | | 9/1998 | Mikus |
| 5,853,384 A | | 12/1998 | Bair |
| 6,017,333 A | | 1/2000 | Bailey |
| 6,083,198 A | * | 7/2000 | Afzal ....................... 604/101.01 |
| 6,123,725 A | | 9/2000 | Aboul-Hosn |
| 6,149,677 A | | 11/2000 | Dobak, III |
| 6,235,019 B1 | | 5/2001 | Lehmann |
| 6,235,048 B1 | | 5/2001 | Dobak, III |
| 6,254,626 B1 | | 7/2001 | Dobak, III |
| 6,261,312 B1 | | 7/2001 | Dobak, III |
| 6,524,268 B2 | * | 2/2003 | Hayner et al. .................... 604/8 |
| 6,622,367 B1 | * | 9/2003 | Bolduc et al. .................. 29/447 |
| 2002/0095115 A1 | * | 7/2002 | Schock ....................... 604/96.01 |

FOREIGN PATENT DOCUMENTS

| | | |
|---|---|---|
| GB | 1 366 631 | 9/1974 |
| WO | WO 98/33535 | 8/1998 |
| WO | WO 01/23030 | 4/2001 |

* cited by examiner

HIGH FLOW-LOW PRESSURE IRRIGATION SYSTEM

This application claims benefit to U.S. Provisional Application Ser. No. 60/329,139 filed Oct. 12, 2001.

BACKGROUND OF THE INVENTION

1. Field of the Invention

The present invention generally relates to renal cooling systems and, more particularly, to a high-flow low-pressure irrigation system for use in minimally invasive surgery.

2. Description of Related Art

Complex renal surgery frequently requires transient interruption of the renal vasculature. Renal hypothermia is known in the field to protect the kidney from ischemia-induced nephron loss and to preserve renal function during partial nephrectomy, renovascular surgery and kidney transplantation. Renal hypothermia is achieved by clamping the renal artery and packing the kidney in ice or slush. Although this practice provides sufficient cooling of the kidney, it presents many drawbacks such as exposing the surrounding structures to the cooling effects of the ice or slush and obscuring the surgical field of view by the ice or slush. Moreover, the practice of packing the kidney in ice or slush is not feasible for minimally invasive or laparoscopic surgery.

With growing interest in laparoscopic surgery, the inability to achieve renal hypothermia during laparoscopic surgery has become a significant problem. Accordingly, there is a need in the art for a renal cooling system for use during minimally invasive surgery and, in particular, a high-flow low-pressure irrigation system.

SUMMARY OF THE INVENTION

The present invention is directed to a high-flow low-pressure irrigation system for directing a fluid to and recovering the fluid from an area within a body. The irrigation system comprises a sheath defining a sheath lumen and a flexible catheter disposed in and through the sheath lumen. The flexible catheter defines a catheter lumen and comprises a plurality of apertures at a distal portion that extends beyond the sheath lumen and spreads in the body area. The fluid is directed and outputted to the body area through the catheter lumen and the apertures, and the outputted fluid is recovered and returned through the sheath lumen. The irrigation system can be endoscopically placed inside a body cavity such as the kidney prior to laparoscopic surgery. The fluid may be a cooling solution such as saline, which is introduced to the irrigation system to allow for preservation of renal tissue during renal artery clamping. A feature of the invention is that only the lumen being irrigated, the catheter lumen, is exposed to the fluid or cooling solution. An advantage of the system of the invention is the fluid or cooling solution can be delivered directly to a very defined space via the catheter lumen while the pressure is kept low by the sheath recovering the outputted fluid. In a renal application, for example, the catheter lumen can deliver the cooling solution directly to the collecting system of the kidney as the access sheath tamponades the ureter and the bladder is completely bypassed. Another feature of the invention is it can be made as a one-piece system that can be easily deployed.

Renal applications of the system include alkaline irrigation for dissolution of uric acid stones, chemo-dissolution of cystine stones, irrigation with chemotherapy drugs after ureteroscopic tumor management, antibiotic irrigation of intra-abdominal abscess and severe infection (e.g., fungal and bacterial), and irrigation of thrombotic agents (Alum or direct delivery of Amicar for renal bleeding).

DESCRIPTION OF THE DRAWINGS

The accompanying drawings, which are included in and constitute a part of this specification, illustrate the embodiments of the invention and, together with the description, explain the features, advantages and principles of the invention. In the drawings.

DESCRIPTION OF PREFERRED EMBODIMENTS AND BEST MODE OF THE INVENTION

Figure 1:
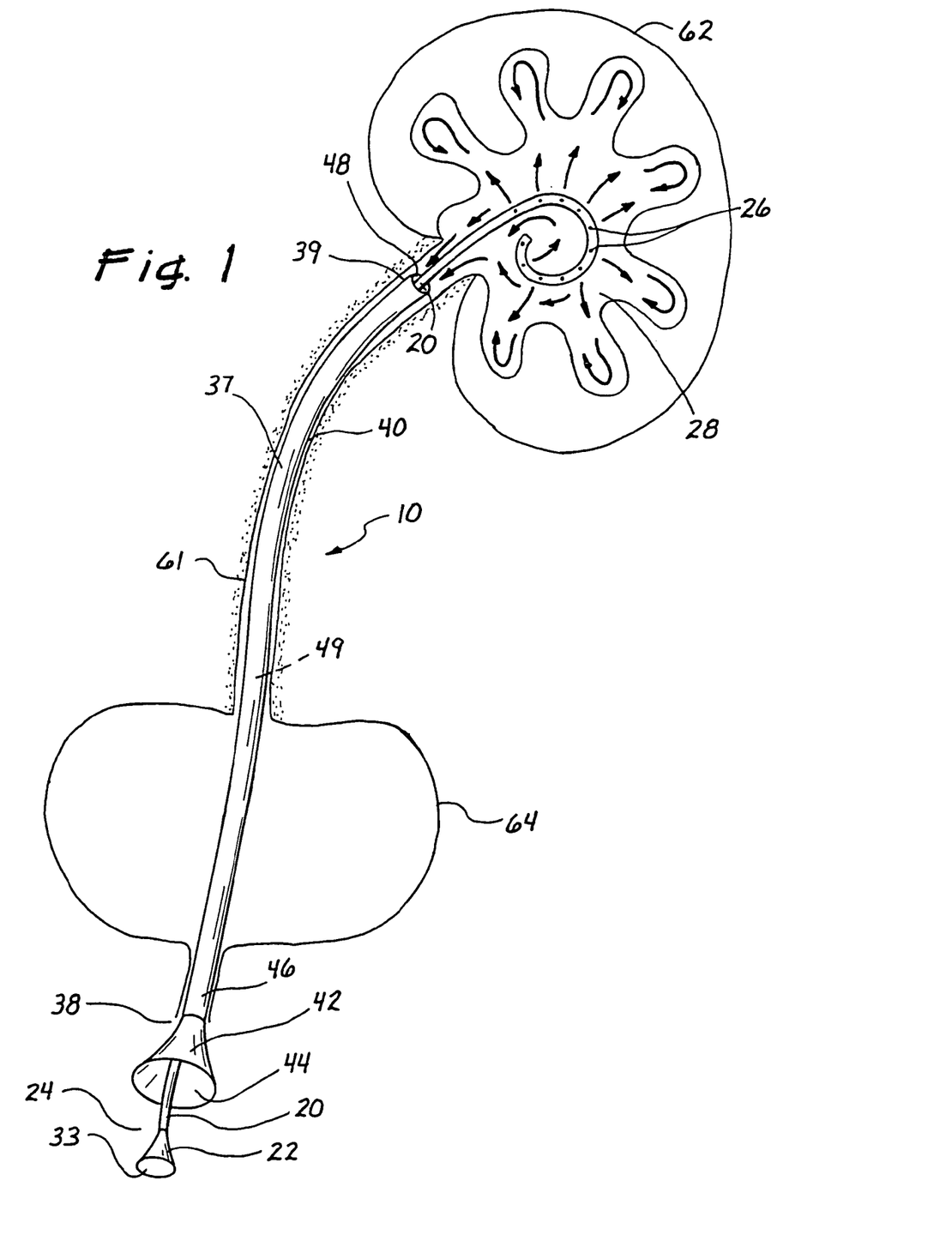
FIG. 1 illustrates a high-flow low-pressure irrigation system in accordance with a first embodiment of the invention.
Figure 2:
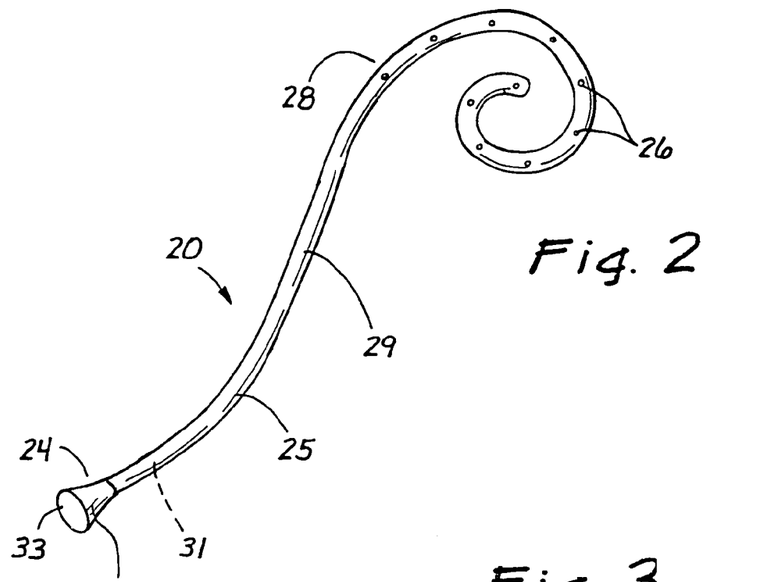
FIG. 2 illustrates a flexible catheter of the irrigation system of the invention.
Figure 4:
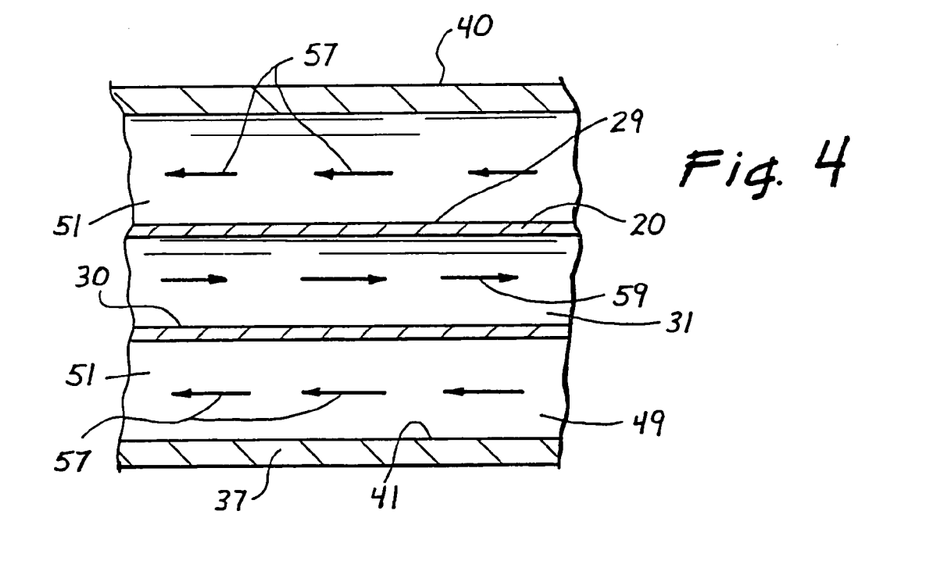
FIG. 4 illustrates the flow of entering fluid and returning fluid in the irrigation system.

FIG. 1 illustrates a high-flow low-pressure irrigation system 10 in accordance with a first embodiment of the invention. System 10 comprises an access sheath 37 and a flexible ureteral catheter 20 disposed inside sheath 37. Sheath 37 includes a sheath outer surface 40 and a sheath inner surface 41 as best illustrated in FIG. 4. Referring back to FIG. 1, a sheath funnel 42 is disposed at a sheath proximal end 38 and includes a sheath proximal opening 44. A sheath tube 46 extends distally from sheath funnel 42 to a sheath distal end 39 where a sheath distal opening 48 is disposed. Sheath tube 46 defines a sheath lumen 49. It is preferable that the length of sheath 37 is less than the length of catheter 20 such that catheter 20 extends through sheath 37 and protrudes out of sheath distal opening 48. In particular, when extended through sheath 37, a distal tube portion 28 of catheter 20 is not enclosed within sheath 37. Referring to FIG. 2, catheter 20 is preferably curled resembling a pigtail at distal portion 28 and may comprise a catheter connector 22 at a proximal end 24. It should be noted that distal portion 28 of catheter 20 may have different configurations to provide optimal irrigation, for example, distal portion 28 may be flared to provide a wide dispersal of irrigant or angled/concentrated to access and irrigate a lower pole stone. Catheter 20 further comprises a thin, flexible tube 25 extending distally from connector 22 and a plurality of distal apertures 26 disposed at distal portion 28.

Catheter 20 is inserted through sheath 37 such that it extends distally out of sheath distal opening 48 at sheath distal end 39. As stated above, distal tube portion 28 pigtails in a preferred embodiment causing distal apertures 26 to spread circularly. Catheter 20 comprises a catheter outer surface 29 and a catheter inner surface 30 as best illustrated in FIG. 4. Catheter 20 defines a catheter lumen 31 that is in fluid communication with a catheter proximal opening 33 and distal apertures 26. A return passageway 51 is defined between catheter outer surface 29 and sheath inner surface 41. Fluid may be introduced into catheter 20, directed through catheter lumen 31, and outputted at distal apertures 26 to contact the target body organ or body area. As additional fluid is continually directed to the body area through catheter lumen 31, the outputted fluid is recovered from the body area by sheath 37. In particular, the outputted fluid enters sheath distal opening 48 and travels through sheath lumen 49 in a proximal direction. Specifically, returning fluid 57 travels in return passageway 51 between catheter outer surface 29 and sheath inner surface 41. Returning fluid 57 does not disrupt entering fluid 59, which is shielded within catheter 20.

Figure 3:
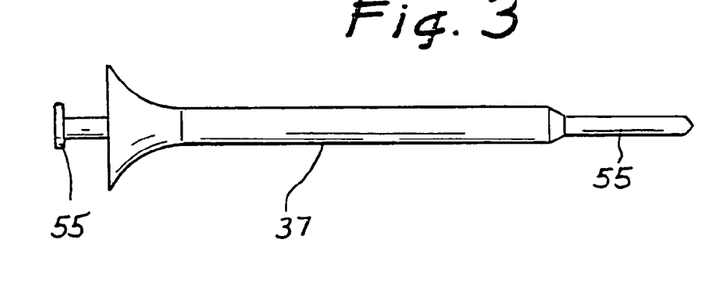
FIG. 3 illustrates an exemplary access sheath for use in the irrigation system.

Sheath 37 may comprise an access sheath similar to those used in connection with dilators or obturators as illustrated in FIG. 3. In a preferred method for irrigating a body organ or cavity, an obturator 55 is inserted through sheath 37 and is manipulated to move and position sheath 37 to a desired location. For example, sheath tube 46 may be placed to extend through a bladder 64 and a ureter 61 as illustrated in FIG. 1. Once sheath 37 is positioned such that sheath distal end 39 is adjacent a target body organ or cavity to be irrigated, obturator 55 may then be removed thereby leaving sheath lumen 49 open for insertion of catheter 20. Catheter 20 is inserted through sheath 37 extending distally from sheath distal end 39.

An advantage of irrigation system 10 of the invention is an irrigant may be introduced into catheter 20 at a high flow rate while maintaining a low pressure in the surrounding area to which the irrigant is directed. For example, an irrigant consisting of $H_2O$ can be pressurized up to 200+ cm while pressure is kept low in the surrounding area by sheath 37 which recovers the outputted irrigant. It will be appreciated that this high-flow low-pressure irrigation system may be used for a multitude of medical and surgical applications. For example, irrigation system 10 may be employed for thermal applications such as renal cooling in laparoscopic surgery. Renal hypothermia may be achieved without incurring the problems of systemic volume expansion or severe hypothermia as commonly found in prior art techniques.

In another application of the invention, the irrigation system may be employed for warming purposes during surgery. For example, irrigation system 10 may be used in connection with cryogenic ablation of a tumor. In this procedure, the target body organ, such as a kidney, is contacted by a cryogenic probe which freezes the contacted portion and surrounding portions of the body organ. Irrigation system 10 of the invention may be used to deliver warm, or at least warmer, fluid to the surrounding area so as to limit the portions of the body organ being frozen. Irrigation system 10 thus facilitates more localized cryo-ablation to minimize damages to healthy portions surrounding the target body organ. The irrigation system of the invention could also be used to cool the kidney, thereby increasing the ablative capabilities of the cryo-ablation device.

Figure 5:
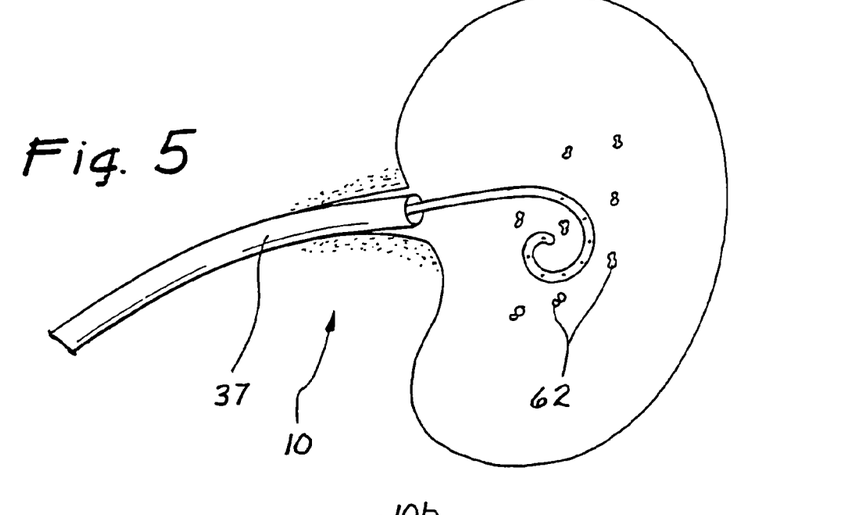
FIG. 5 illustrates the irrigation system flushing out stone fragmentations from a body cavity.

In a further aspect of the invention, irrigation system 10 may be employed for simply irrigating a body area. For example, irrigation system 10 may be used to flush out stone fragmentations 62 from a particular area as illustrated in FIG. 5. Sheath 37 may be provided with a greater diameter, if necessary, to accommodate recovery of larger fragmentations. Other renal applications include alkaline irrigation for dissolution of uric acid stones, chemo-dissolution of cystine stones, irrigation with chemotherapy drugs after ureteroscopic tumor management, antibiotic irrigation of intra-abdominal abscess and severe infection (e.g., fungal and bacterial), and irrigation of thrombic agents.

It should be noted that the irrigation system of the invention may be adapted for use outside of the upper urinary tract. For example, system 10 may be used in connection with continuous bladder irrigation and stomach lavage. In another example, system 10 may be used in central nervous applications such as to clear a severe central nervous system infection. In yet another example, system 10 of the invention may be used for intra-uterine irrigation in treating endometriosis. Similarly, system 10 may be used in treating severe hypothermia in connection with a lavage using warmed irrigant to increase core body temperature.

From the foregoing description, it will be appreciated that the fluid used in the system of the invention may comprise a variety of different types depending upon the application. The fluid may comprise a saline solution set at certain temperatures for thermal applications. For other applications such as dissolution, the fluid may contain a chemical solution adapted to accomplish its specific objective.

Figure 6:
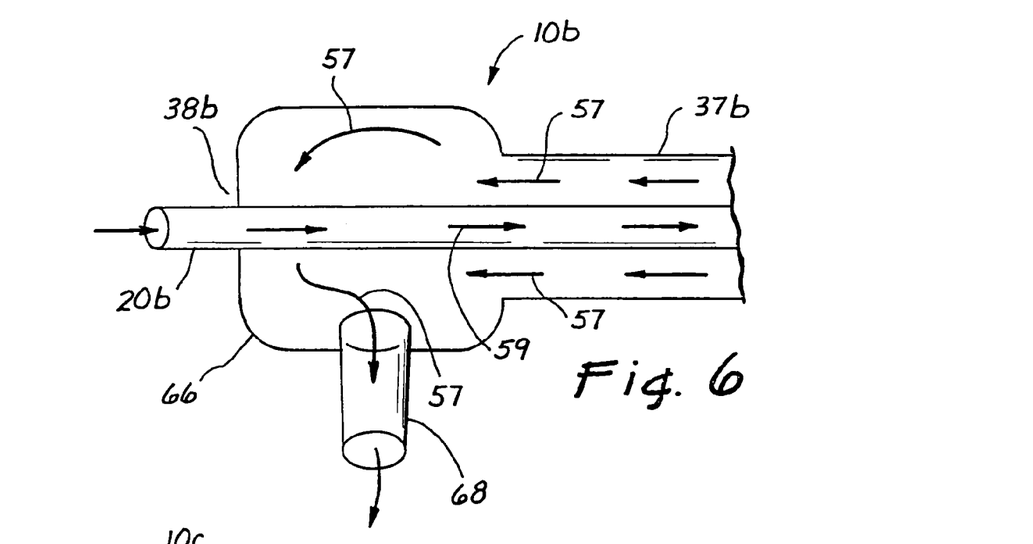
FIG. 6 illustrates a high-flow low-pressure irrigation system in accordance with a second embodiment of the invention.
Figure 7:
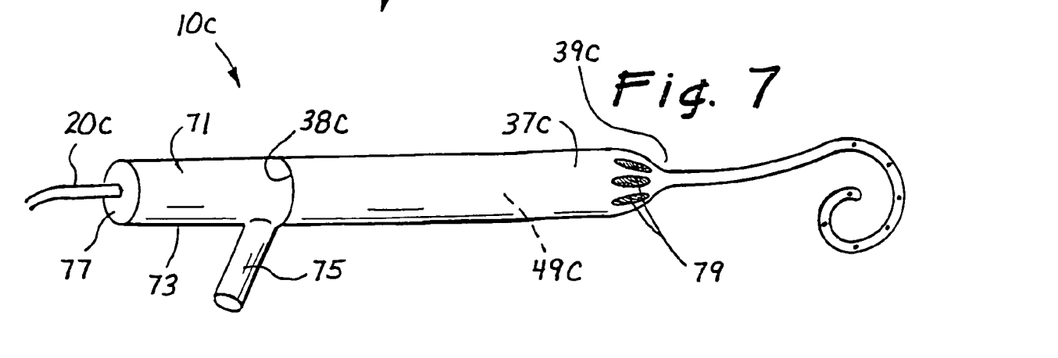
FIG. 7 illustrates a high-flow low-pressure irrigation system in accordance with a third embodiment of the invention.

FIG. 6 illustrates a high-flow low-pressure irrigation system 10b in accordance with a second embodiment of the invention. Irrigation system 10b comprises an access sheath 37b and a flexible ureteral catheter 20b disposed inside the access sheath 37b. Sheath 37b is unique in that in that it has a hub 66 at a sheath proximal end 38b. Hub 66 forms a seal with catheter 20b and includes an exit port or exit tube 68 for directing returning fluid 57 outward. In another embodiment of the invention, an irrigation system 10c may include a proximal Y-fitting hub 71 as illustrated in FIG. 7. Y-fitting hub 71 includes a first tube 73 adapted for receiving a flexible catheter 20c and a second tube 75 adapted for directing the returning fluid outward. Both tubes 73 and 75 are in fluid communication with each other and sheath lumen 49c. Tube 73 includes a proximal tube end 77 that forms a seal with flexible catheter 20c to prevent the returning fluid from spilling.

In a preferred embodiment of system 10c, the system is provided as a one-piece device where a sheath 37c is secured to Y-fitting hub 71 at a sheath proximal end 38c and forms a seal around flexible catheter 20c at a sheath distal end 39c. It is understood that such a seal may be formed in a variety of ways. For example, sheath 37c may be adhered or welded to catheter 20c at sheath distal end 39c. Sheath apertures or ports 79 are provided adjacent to sheath distal end 39c to enable the outputted fluid to return to sheath lumen 49c.

Figures 8, 9:
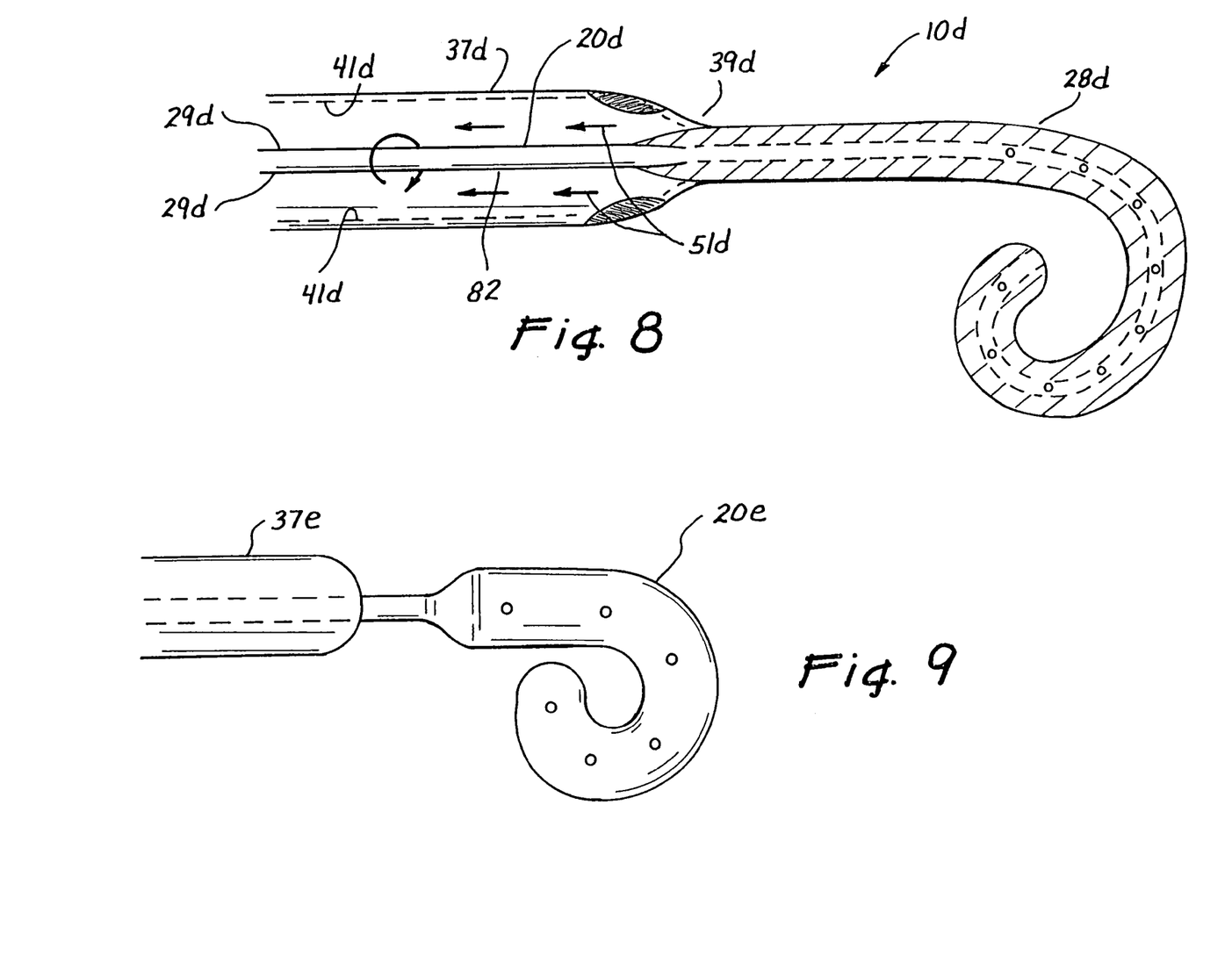
FIG. 8 illustrates a high-flow low-pressure irrigation system in accordance with a fourth embodiment of the invention.
FIG. 9 illustrates another embodiment of the flexible catheter of the irrigation system.

In yet another embodiment of the invention, an irrigation system 10d is provided as one unit including a catheter 20d and a sheath 37d as illustrated in FIG. 8. Specifically, catheter 20d is coupled to sheath 37d at sheath distal end 39d. The cross-sectional area occupied by catheter 20d within sheath 37d may be minimized to optimize the flow of the returning fluid. Similar to irrigation systems discussed above, system 10d may be used for dissolving and recovering stone fragments. Within sheath 37d, recovery of the returning fluid and stone fragments can be optimized by providing a larger gap between an inner surface 41d of sheath 37d and an outer surface 29d of catheter 20d. Outside of sheath 37d, a catheter distal portion may have a wall thickness that is greater than the wall thickness of portion 82 disposed within sheath 37d so as to provide greater column strength and kink resistance.

It should be reminded that conventional catheters are designed to operate as stand-alone devices. As such, conventional catheters need to have bodies having sufficient column strength and kink resistance. With irrigation system 10*d*, however, catheter portion 82 within sheath 37*d* does not need to meet the same performance requirements with regard to column strength and kink resistance as the conventional catheters because portion 82 is protected by sheath 37*d*. As a result, the wall thickness of shielded portion 82 may be minimized thereby maximizing the cross-sectional area of return passageway 51*d*.

Figure 10:
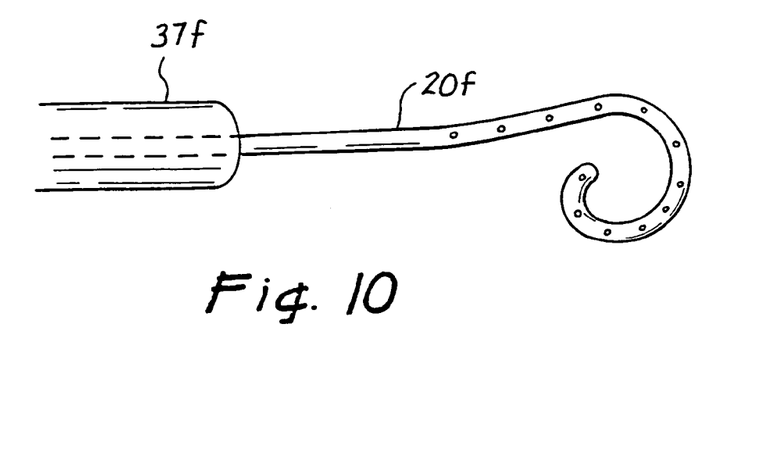
FIG. 10 illustrates yet another embodiment of the flexible catheter of the irrigation system.

FIGS. 9 and 10 illustrate that catheters 20*e* and 20*f* for use with separate sheaths 37*e* and 37*f*, respectively, may still have thin walls. That is, whether a catheter is affixed to or separate from a sheath, the sheath provides the irrigation system with the necessary column strength and kink resistance so as to enable the catheter to be thinned. In FIG. 9, the wall of catheter 20*e* has a thickness that expands outside of sheath 37*e* while in FIG. 10, the wall of catheter 20*f* has a thickness that remains substantially the same within and outside of sheath 37*f*.

Figure 11:
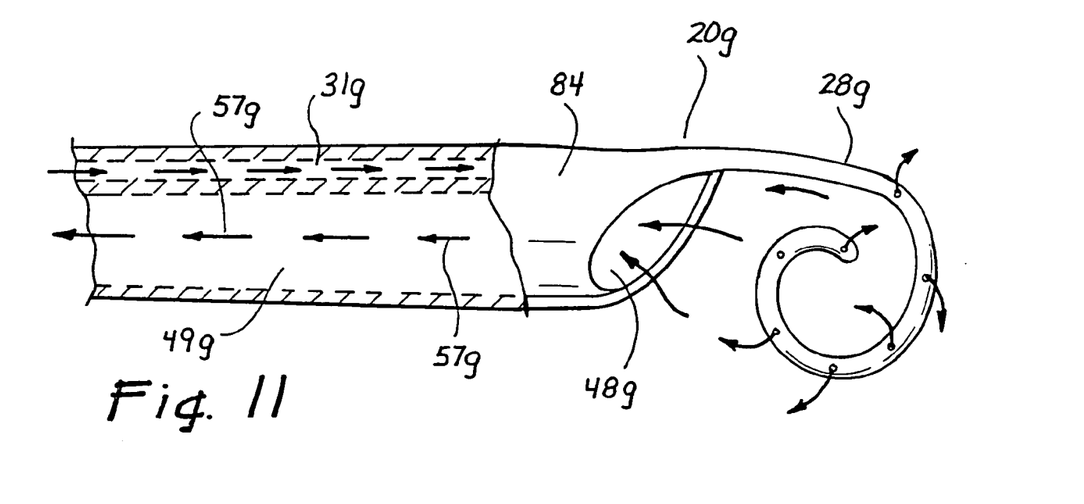
FIG. 11 illustrates a high-flow low-pressure irrigation system having an integrated catheter and access sheath in accordance with another embodiment of the invention.
Figure 12:
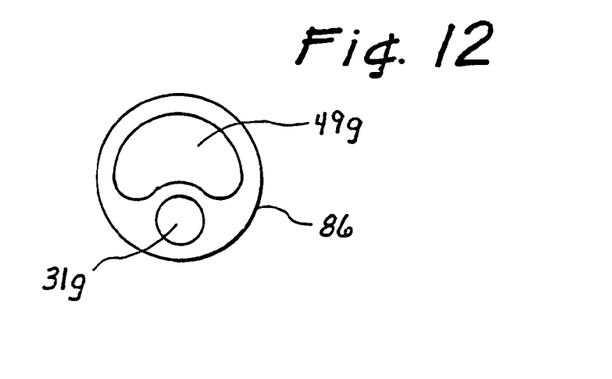
FIG. 12 illustrates a cross-sectional view of the integrated catheter and access sheath of the irrigation system of FIG. 11.

FIGS. 11 and 12 illustrate another embodiment of a high-flow low-pressure irrigation system 20*g* comprising a multi-lumen conduit 84 operating both as a sheath and a catheter. Conduit 84 comprises a common wall 86 that forms a catheter lumen 31*g* and a sheath lumen 49*g* (see FIG. 12). Catheter lumen 31*g* provides a path for the inflow of fluid to a target body area and sheath lumen 49*g* provides a path for the outflow or returning fluid from the target body area. The outflow of fluid is maximized as catheter lumen 31*g* can be minimized to occupy a smaller cross-sectional area. Catheter lumen 31*g* is sealed from sheath lumen 49*g* and is further defined by a catheter distal portion 28*g* extending distally from conduit 84. Conduit 84 includes a distal opening 48*g* in fluid communication with sheath lumen 49*g*. Blunt obturators and other instrumentation may be inserted through the large sheath lumen 49*g* defined by conduit 84 for placement of irrigation system 20*g*.

It will be appreciated that each embodiment of the invention is preferably configured such that only the target body organ or area being irrigated is exposed to the fluid. An input conduit and an output conduit are provided for flushing and draining, respectively, of the fluid. In the above embodiments, the input conduit is a catheter disposed adjacent to or inside the lumen of the output conduit, which is a sheath. It is anticipated, however, that the input conduit may be a sheath flushing an irrigating fluid and the output conduit may be an internal catheter draining the irrigating fluid. In such an embodiment, a pressure transducer may be used in the internal catheter so if or when the intravenal pressure reaches a set level, e.g., 30 cm H2O, the flow of the irrigating fluid could be automatically stopped. The lumen of the input conduit is shielded from the lumen of the output conduit such that the flushing fluid and draining fluid do not disrupt each other's flow. The input conduit generally has a distal portion that projects out from the output conduit. The distal portion of the input conduit includes apertures for directing the fluid to the target body area. The outputted fluid is recovered through a lumen having an opening or apertures at its distal end. It is foreseeable that the internal catheter and/or sheath is capable of sensing and recording pressure in the renal pelvis so as to adjust the flow of flushing and draining fluid in the irrigation system.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention.

The invention claimed is:

1. A high-flow low-pressure irrigation system for directing a fluid to and recovering the fluid from an area within a body, comprising:
   a sheath defining a sheath lumen with a sheath distal opening at a distal end of the sheath; and
   a flexible catheter disposed in and through the sheath lumen, said flexible catheter defining a catheter lumen and comprising a plurality of apertures at a distal portion that extends beyond the sheath lumen and spreads in the body area,
   wherein an irrigation fluid is directed and outputted to the body area through the catheter lumen and the apertures,
   wherein the distal portion of the flexible catheter is shaped to curve back towards a proximal portion of the flexible catheter and towards the sheath distal opening at the distal end of the sheath in that the fluid outputted from the plurality of apertures at the distal portion of the flexible catheter to the body area is returned through the sheath distal opening at the distal end of the sheath, and
   wherein the distal portion is shaped into a pigtail configuration.

2. The high-flow low-pressure irrigation system of claim 1, wherein the distal portion is shaped into a flared configuration providing a wide dispersal of the fluid in the body area.

3. The high-flow low-pressure irrigation system of claim 1, wherein the distal portion is configured to access and irrigate any part of a kidney.

4. The high-flow low-pressure irrigation system of claim 1, wherein the distal portion is configured to access and irrigate a lower pole stone in a kidney.

5. The high-flow low-pressure irrigation system of claim 1, wherein the catheter lumen is in fluid communication with a catheter proximal opening and the apertures.

6. The high-flow low-pressure irrigation system of claim 1, wherein the catheter further comprises a catheter connector at a catheter proximal end.

7. The high-flow low-pressure irrigation system of claim 6, wherein the catheter comprises a flexible tube extending distally from the catheter proximal end, said flexible tube including the apertures at the distal portion.

8. The high-flow low-pressure irrigation system of claim 1, wherein the catheter includes a catheter outer surface and a catheter inner surface.

9. The high-flow low-pressure irrigation system of claim 8, wherein the sheath comprises:
   a sheath funnel disposed at a sheath proximal end and having a sheath proximal opening; and
   a sheath tube extending distally from the sheath funnel to a sheath distal end where the sheath distal opening is disposed.

10. The high-flow low-pressure irrigation system of claim 9, wherein the sheath comprises a sheath outer surface and a sheath inner surface.

11. The high-flow low-pressure irrigation system of claim 9, wherein the sheath is shorter than the catheter.

12. The high-flow low-pressure irrigation system of claim 10, wherein the catheter outer surface and the sheath inner surface define a return passageway.

13. The high-flow low-pressure irrigation system of claim 9, further comprising an obturator for moving and positioning the sheath to a desired location within the body.

14. The high-flow low-pressure irrigation system of claim 13, wherein the sheath is positioned such that the sheath distal end is adjacent to or inside a desired body area to be irrigated.

15. The high-flow low-pressure irrigation system of claim 1, wherein the distal portion spreads the apertures circularly.

16. The high-flow low-pressure irrigation system of claim 9, wherein the returning fluid enters the sheath distal opening and travels through the sheath lumen in a proximal direction.

17. The high-flow low-pressure irrigation system of claim 12, wherein the returning fluid travels in the return passageway and does not disrupt the entering fluid, which is shielded within the catheter lumen.

18. The high-flow low-pressure irrigation system of claim 1, wherein the fluid is introduced into the catheter lumen at a constant flow rate while maintaining a low pressure in a surrounding area to which the fluid is directed.

19. The high-flow low-pressure irrigation system of claim 1, wherein the fluid prior to being directed through the catheter lumen is pressurized up to 200 cm.

20. The high-flow low-pressure irrigation system of claim 18, wherein the pressure is kept low by the sheath recovering the returning fluid.

21. The high-flow low-pressure irrigation system of claim 1, wherein the system is employed in minimally invasive surgery.

22. The high-flow low-pressure irrigation system of claim 18, wherein the fluid introduced into the catheter lumen is warmer than fluid in the surrounding area.

23. The high-flow low-pressure irrigation system of claim 18, wherein the fluid introduced into the catheter lumen is cooler than fluid in the surrounding area.

24. The high-flow low-pressure irrigation system of claim 1, wherein the system is employed to flush out stone fragmentations from the body area.

25. The high-flow low-pressure irrigation system of claim 1, wherein the fluid comprises a saline solution.

26. The high-flow low-pressure irrigation system of claim 1, wherein the sheath comprises a hub disposed at a sheath proximal end and having an exit port for directing the returning fluid outward of the sheath.

27. The high-flow low-pressure irrigation system of claim 26, wherein the hub includes a Y-fitting component.

28. The high-flow low-pressure irrigation system of claim 9, wherein the sheath forms a seal around the catheter at the sheath distal end.

29. The high-flow low-pressure irrigation system of claim 28, further comprising a plurality of sheath apertures disposed peripherally around the seal to recover and direct the returning fluid to the sheath lumen.

30. A high-flow low-pressure irrigation system for directing a fluid to and recovering the fluid from an area within a body, comprising:
a sheath defining a sheath lumen having a proximal end and a distal end with an aperture at the distal end aligned with the sheath lumen; and
a flexible catheter coupled to the sheath, said catheter having a first section with a proximal end and a distal end disposed inside the sheath lumen and a second section disposed outside the sheath lumen, said catheter defining a catheter lumen and comprising a plurality of apertures at a distal portion,
wherein an irrigation fluid is directed and outputted to the body area through the catheter lumen and the apertures,
wherein the distal end of the first section is fixed at the distal end of the sheath lumen and at the aperture of the sheath in that the fluid outputted to the body area is returned through the sheath lumen through the aperture of the sheath,
wherein the catheter has a column strength that is less than the column strength of the sheath and the sheath is more kink resistant than the catheter such that the catheter is configured to access and irrigate any part of a kidney.

31. The high-flow low-pressure irrigation system of claim 30, wherein the first section of the catheter has a wall having a first thickness and the second section of the catheter has a wall having a second thickness that is thicker than the first wall thickness.

32. The high-flow low-pressure irrigation system of claim 30, wherein the sheath forms a seal around the catheter at one of a distal end of the first section and a proximal end of the second section.

33. The high-flow low-pressure irrigation system of claim 30, wherein the distal portion of the catheter curls in a pigtail configuration.

34. The high-flow low-pressure irrigation system of claim 30, wherein the distal portion of the catheter spreads in a flared configuration.

35. A high-flow low-pressure irrigation system for directing a fluid to and recovering the fluid from an area within a body, comprising:
a monolithic multi-lumen conduit having an inner surface and defining a first lumen and a second lumen adjacent the first lumen, said multi-lumen conduit comprising a plurality of apertures at a distal portion of the first lumen and at least one aperture at a distal portion of the second lumen,
wherein the first lumen is in fluid communication with the apertures,
wherein the fluid communication is a direct fluid output through the first lumen to the apertures, and
wherein the first lumen is formed along the inner surface of the multi-lumen conduit and a distal most aperture of the plurality of apertures of the first lumen is positioned proximate the at least one aperture of the second lumen the fluid outputted from the plurality of apertures of the first lumen to the body area is returned through the at least one aperture of the second lumen;
wherein the distal portion of the first lumen has a closed distal end and extends farther than and beyond a distal end of the distal portion of the second lumen.

36. The high-flow low-pressure irrigation system of claim 35, wherein the distal portion curls in a pigtail configuration.

37. The high-flow low-pressure irrigation system of claim 35, wherein the distal portion spreads in a flared configuration.

38. The high-flow low-pressure irrigation system of claim 35, wherein the distal portion is configured to access and irrigate any part of a kidney.

39. The high-flow low-pressure irrigation system of claim 35, wherein the cross-sectional area of the first lumen is less than the cross-sectional area of the second lumen.

40. The high-flow low-pressure irrigation system of claim 35, wherein the first lumen having a plurality of apertures and the second lumen having only a single aperture being larger in diameter than each of the plurality of apertures in the first lumen.

41. The high-flow low-pressure irrigation system of claim 35, wherein the plurality of apertures are located only in a portion of the first lumen that extends beyond the second lumen.

* * * * *